(12) United States Patent
Hilbert et al.

(10) Patent No.: US 11,398,027 B2
(45) Date of Patent: Jul. 26, 2022

(54) AGE-SPECIFIC IMAGE ATLAS

(71) Applicant: SIEMENS HEALTCARE GMBH, Erlangen (DE)

(72) Inventors: Tom Hilbert, Lausanne (CH); Tobias Kober, Lausanne (CH)

(73) Assignee: Siemens Healthcare GmbH, Erlangen (DE)

(*) Notice: Subject to any disclaimer, the term of this patent is extended or adjusted under 35 U.S.C. 154(b) by 177 days.

(21) Appl. No.: 16/835,609

(22) Filed: Mar. 31, 2020

(65) Prior Publication Data

US 2020/0320691 A1 Oct. 8, 2020

(30) Foreign Application Priority Data

Apr. 5, 2019 (EP) .................................... 19167587

(51) Int. Cl.
*G06K 9/00* (2022.01)
*G06T 7/00* (2017.01)
*G06T 7/136* (2017.01)
*G06T 7/38* (2017.01)
*G16H 10/60* (2018.01)
*G16H 50/30* (2018.01)
*G06N 20/10* (2019.01)

(52) U.S. Cl.
CPC .......... *G06T 7/0012* (2013.01); *G06N 20/10* (2019.01); *G06T 7/136* (2017.01); *G06T 7/38* (2017.01); *G16H 10/60* (2018.01); *G16H 50/30* (2018.01); *G06T 2207/10088* (2013.01); *G06T 2207/20128* (2013.01); *G06T 2207/30004* (2013.01); *G06T 2211/424* (2013.01)

(58) Field of Classification Search
CPC .................................................... G06T 7/0012
See application file for complete search history.

(56) References Cited

U.S. PATENT DOCUMENTS

| 9,471,978 B2* | 10/2016 | Chen ..................... G16H 20/10 |
| 2015/0141804 A1* | 5/2015 | Rooney ................ A61B 5/0263 600/419 |
| 2017/0039714 A1* | 2/2017 | Small ....................... G06T 5/50 |

(Continued)

OTHER PUBLICATIONS

Fillmore et al. (NPL "Age-specific MRI brain and head templates for healthy adults from 20 through 89 years of age", Published Apr. 8, 2015, Aging Neuroscience) (Year: 2015).*

(Continued)

*Primary Examiner* — Oneal R Mistry
(74) *Attorney, Agent, or Firm* — Laurence A. Greenberg; Werner H. Stemer; Ralph E. Locher

(57) ABSTRACT

A method and a system create an age-specific quantitative atlas for a biological object. The method includes obtaining a quantitative map of the biological object for each subject of a healthy subject population, generating an age-specific initial map for the biological object using a weighted mean, and spatially registering each of the quantitative maps on the age-specific initial map. The generating and registering steps are repeated iteratively until reaching a first predefined alignment threshold between all spatially registered quantitative maps. The new age-specific initial map obtained is stored at the end of the iterative process of the repeating step as the age-specific quantitative atlas for a biological object characterized by the specific age.

8 Claims, 2 Drawing Sheets

(56) References Cited

U.S. PATENT DOCUMENTS

2017/0069086 A1 3/2017 Li et al.
2017/0357753 A1* 12/2017 Mori .................. A61B 5/055
2018/0310869 A1* 11/2018 Yablonskiy ...... G01R 33/56366

OTHER PUBLICATIONS

Filmore, "Age-specific MRI brain and head templates for healthy adults from 20 through 89 years of age" (Year: 2015).*

Piredda, Gian F. et al.: "Quantitative T1 and T2 Brain Atlases for the Detection of Abnormal Relaxation Times", Clinical Imaging Technology, Proc. Intl. Mag. Reson. Med. 26 (2018).

Sumpf, Tilman J. et al.: "Model-Based Nonlinear Inverse Reconstruction for T2 Mapping Using Highly Undersampled Spin-Echo MRI", Journal of Magnetic Resonance Imaging, 2011, vol. 34, pp. 420-428, DOI 10.1002/jmri.22634.

Deoni, Sean C. L.: "Quantitative Relaxometry of the Brain", NIH Public Access, Top Magn Reson Imaging, Apr. 2010, vol. 21, No. 2, pp. 101-113, doi:10.1097/RMR.0b013e31821e56d8.

Wu, Guorong et al: "5 Emergence of Groupwise Registration in MR Brain Study" In: "Biosignal Processing : Principles and Practices", CRC Press LLC, XP055622220, ISBN: 978-1-4398-7144-7; pp. 5-1, Section "5.3 Population Center-Guided Groupwise Registration"; Figure 5.5; 2012.

Marques, Jose P. et al.: "MP2RAGE, a self bias-field corrected sequence for improved segmentation and T1-mapping at high field", NeuroImage, 2010, vol. 49, pp. 1271-1281, doi:10.1016/j.neuroimage 2009.10.002.

Fonov, Vladimir et al.: "Unbiased Average Age-Appropriate Atlases for Pediatric Studies", NeuroImage, Jan. 1, 2011, vol. 54, pp. 313-327, doi: 10.1016/j.neuroimage.2010.07.033.

Avants, Brian et al.: "Geodesic estimation for large deformation anatomical shape averaging and interpolation", NeuroImage, 2004, vol. 23, pp. 139-150, doi:10.1016/j.neuroimage.2004.07.010.

Bonnier, Guillaume et al.: "Advanced MRI unravels the nature of tissue alterations in early multiple sclerosis", Annals of Clinical and Translational Neurology, 2014, vol. 1, No. 6, pp. 423-432, doi: 10.1002/acn3.68.

Klein, Stefan et al.: "A Toolbox for Intensity-Based Medical Image Registration", IEEE Transactions on Medical Imaging, Jan. 2010, vol. 29, No. 1, pp. 196-205.

Ma, Dan et al.: "Magnetic resonance fingerprinting", Nature, Mar. 14, 2013, vol. 495, pp. 187-192 doi:10.1038/nature11971.

* cited by examiner

AGE-SPECIFIC IMAGE ATLAS

CROSS-REFERENCE TO RELATED APPLICATION

This application claims the priority, under 35 U.S.C. § 119, of German application EP 19 167 587.5, filed Apr. 5, 2019; the prior application is herewith incorporated by reference in its entirety.

BACKGROUND OF THE INVENTION

Field of the Invention

The present disclosure is directed, in general, to imaging techniques for imaging biological objects, like tissues, and more specifically to the creation of normative atlases, using notably magnetic resonance imaging (MRI).

Within the context of classical MRI, the contrast apparent is the result of a combination of different physical parameters of the imaged tissue, the particular MRI acquisition technique and its parameters.

A different approach of acquiring MRI-based information on biological tissue is to directly measure one or more of its underlying physical properties, e.g. the tissue-specific relaxation constants T1 and T2 or the proton density PD. Those quantitative techniques are usually referred to as "parametric mapping" or "quantitative imaging" methods. Using this approach, the resulting image contrasts become more independent from the employed hardware, the applied imaging technique and the particular imaging parameters, because they directly probe the properties of the tissue, facilitating comparability. In other words, it provides the means to move from relative contrast information depending on many different factors towards an absolute measure of one or more separate physical properties.

Over the past decades, various fast quantitative imaging methods to measure relaxation times were developed (see for instance Marques et al., MP2RAGE, A Self Bias-Field Corrected Sequence for Improved Segmentation and T1-Mapping at High Field, Neuroimage 2010, 49(2):1271-1281). To unfold the clinical potential of quantitative measures, atlases of normal values and methods to compare measurements from a single patient to these atlases are desirable.

These atlases describe the expected distribution (e.g. described by the mean and standard deviation) of a quantitative value at a specific spatial location in a healthy subject. For illustration, one could for example compare a quantitative MR measurement at a specific location in the left frontal temporal grey matter measured in the brain of a patient to the "expected" healthy value; apparent statistically significant differences hint to an underlying tissue alteration at this location, possibly caused by a pathological process. The comparison with an atlas hence provides a direct aid to a clinician to diagnosis. Notably, an atlas may also include a more complex model with depending variables, e.g. a linear model which describes the mean and standard deviation in a healthy subject depending on the variables: age and sex.

Typically, to ensure the spatial specificity, these atlases are generated by co-registering the quantitative maps of a healthy cohort (i.e. a dataset of healthy subjects) into a common space (sometimes referred to as "spatial normalization"). By the end of this co-registration, the shape of the organ under investigation (e.g. brain) can be seen as averaged across the healthy cohort.

Ideally, the healthy-cohort data used to generate the atlas spans over a wide age range to be able to differentiate between tissue changes driven by aging and those driven by disease. This is due to limitations of the co-registration; if age-related morphological differences of the organ are too large, the co-registration can fail. The co-registration of images (averaging of organ shape) from both young and elderly subjects into a common space may hence not be ideal.

In particular, the co-registration (spatial normalization) of quantitative maps obtained from elderly and young subjects may lead to a loss of information in shape due to an averaging effect across a wide age range. Usually, this technical problem is ignored when creating quantitative atlases, independently of the imaging technique used.

SUMMARY OF THE INVENTION

While the present invention has been introduced within the context of MRI, it is an objective of the present invention to propose a method and a system capable of automatically creating a quantitative atlas from a healthy cohort, the method and technique being not restricted to the field of MRI, but also suitable for different imaging techniques for imaging biological objects like computed tomography, positron emission tomography, single proton emission computed tomography, ultrasound, etc., wherein the method and system overcome the previously mentioned problems.

The objective is achieved according to the present invention by a method and a system for automatic creation of a quantitative atlas according to the object of the independent claims. Dependent claims present further advantages of the invention.

The present invention proposes notably to create a more accurate quantitative atlas compared to existing quantitative atlases by not only taking into account age-dependent, microstructural tissue changes (e.g. increase in T1 and/or T2 in case of MRI), but also macrostructural organ shapes (e.g. head size). Since the patient's organ shape will be much closer to an atlas from healthy people of the patient's age, the co-registration performs then better, and the tissue model is better adapted, leading thus to a better detection of tissue alterations.

The present invention proposes therefore a method for automatically creating a quantitative atlas for a biological object, wherein the quantitative atlas accounts for changes in quantitative value (like T1 relaxation in the case of MRI) and for a change in a biological object shape depending on the age of the biological object. The disclosed method provides notably the clinical advantage of improving a differentiation between age and disease effects.

The present invention proposes also a system for carrying out the previously described method.

The foregoing has outlined rather broadly the features and technical advantages of the present disclosure so that those skilled in the art may better understand the detailed description that follows. In particular, the present invention may help a physician to diagnose a disease for a biological object, which is typically an organ, like a brain.

Additional features and advantages of the disclosure will be described hereinafter that form the object of the claims. Those skilled in the art will appreciate that they may readily use the concept and the specific embodiment disclosed as a basis for modifying or designing other structures for carrying out the same purposes of the present disclosure. Those skilled in the art will also realize that such equivalent constructions do not depart from the spirit and scope of the disclosure in its broadest form.

Other features which are considered as characteristic for the invention are set forth in the appended claims.

Although the invention is illustrated and described herein as embodied in an age specific atlas, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Figure 1:
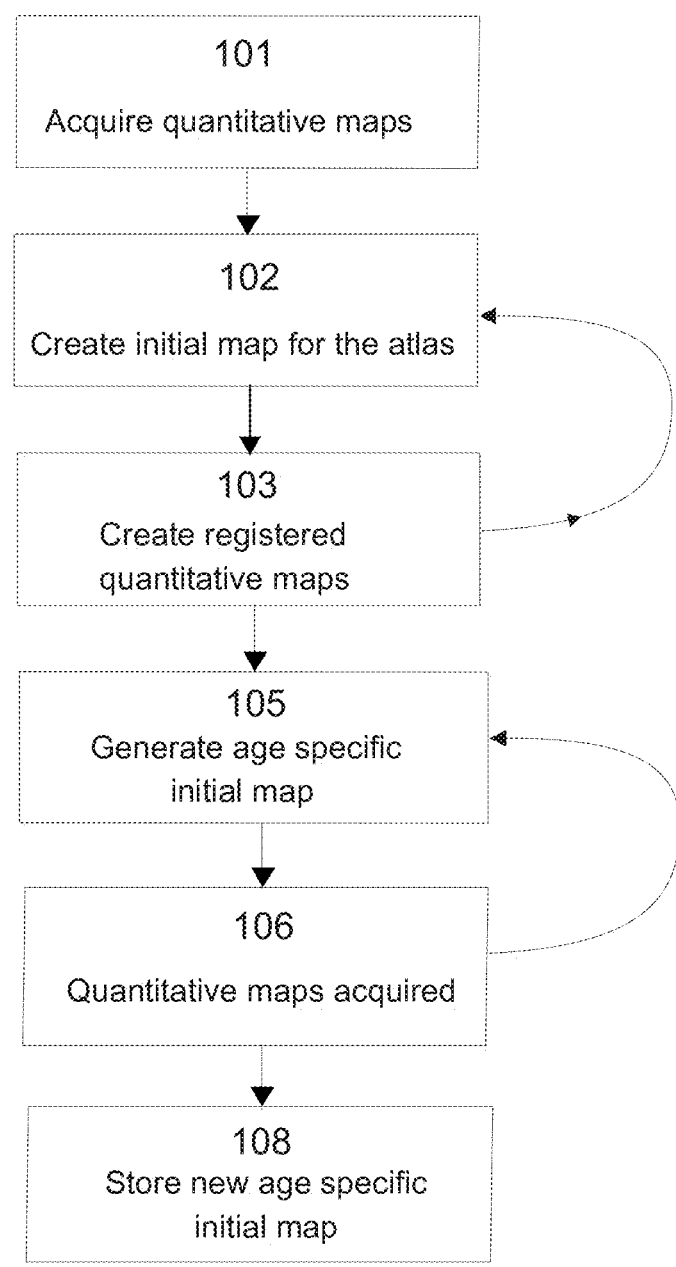
FIG. 1 is a flowchart of a method for creating an age-specific atlas according to the invention.
Figure 2:
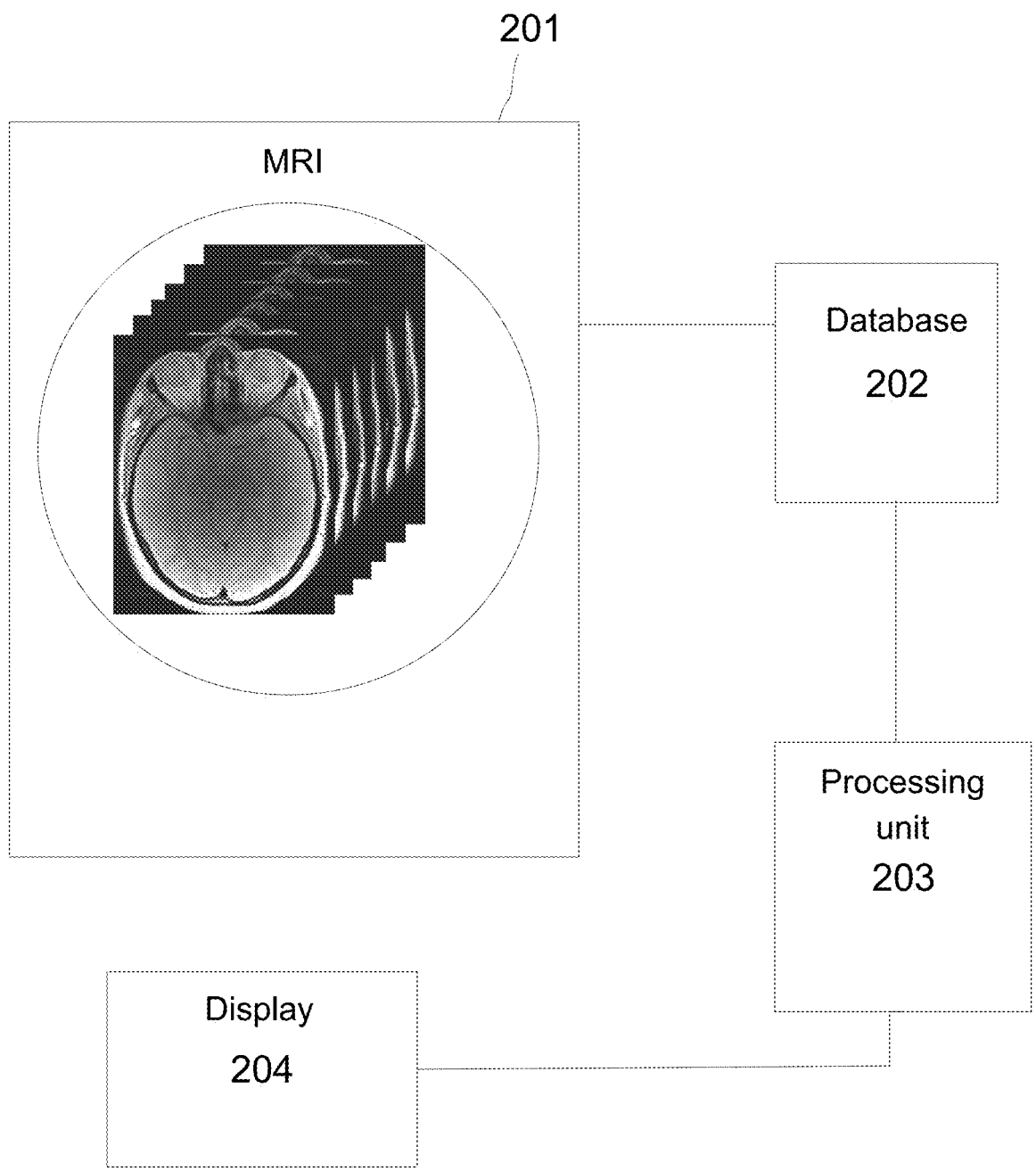
FIG. 2 is an illustration of a system for implementing the claimed method.

FIGS. 1 and 2, discussed below, and the various embodiments used to describe the principles of the present disclosure in this patent document are by way of illustration only and should not be construed in any way to limit the scope of the disclosure. Those skilled in the art will understand that the principles of the present disclosure may be implemented in any suitably arranged device. The numerous innovative teachings of the present application will be described with reference to exemplary non-limiting embodiments.

Referring now to the figures of the drawings in detail and first, particularly to FIG. 1 thereof, there is shown different steps of a method 100 carried out by a system according to the invention for creating, preferentially automatically creating, an age-specific quantitative atlas for a biological object, like a brain, wherein the age-specific quantitative atlas makes it possible to compare quantitative values of a parameter measured for an investigated biological object with the quantitative values of the parameter obtained for the age-specific quantitative atlas. The method 100 contains notably the following successive steps, which are preferentially automatically performed by the system according to the invention:

At step 101, a quantitative map of the biological object is acquired or obtained for each subject of a healthy subject population. The quantitative maps might be acquired or obtained using a medical device such as an X-ray equipment or an MRI apparatus or any other device enabling to acquire a quantitative map of the biological object. The quantitative maps might also be acquired from a database used for storing quantitative maps. Each quantitative map is a map or image of the biological object containing or showing quantitative values for a parameter measurable for the biological object. All quantitative maps are maps showing values for the parameter, i.e. quantitative maps showing values for the same parameter are used hereafter. Optionally, the parameter might be obtained by combining several other measurable parameters. For instance, in the field of MRI, a typical quantitative map might be a T1 image or PD image or a combination of both.

Optionally, the system may then carry out steps 102-104, or directly continue with step 105.

At step 102, an initial map for the atlas is created by averaging map (i.e. image) intensities across all previously acquired or obtained quantitative maps for the biological object.

Then, at step 103, a registered quantitative map is created for each of the quantitative maps by spatially registering the quantitative map on the initial map using a registration algorithm such as ELASTIX or similar. Optionally, an affine registration (i.e. only rotation, translation, scaling and shear) may be used in step 103 to account for differences in organ size and alignment between the subjects (at this stage, it is not intended to change the organ shape).

Then, at step 104, steps 102 and 103 are iteratively repeated so that at each iteration a new initial map for the atlas is created by averaging the intensities across all registered quantitative maps, i.e. all previously obtained spatially registered quantitative maps, and the previously registered quantitative maps are then spatially registered on the new initial map, until reaching a predefined alignment threshold between all registered quantitative maps. The creation of an atlas according to the invention by repeatedly averaging intensities and then registering on the "averaged intensity map" each of the quantitative maps for the biological object makes it possible to iteratively improve the biological object alignment between the subjects of the healthy subject population.

At step 105, the system according to the invention is configured for generating an age-specific initial map using a weighted mean of the values of the quantitative maps obtained at the previous step. Preferentially, a contribution to the weighted mean of values of quantitative maps obtained at the previous step (e.g. already registered or not yet registered) depends on an age difference between the age of the biological object from which the quantitative map value is considered for averaging and a specific age As, wherein by "age difference" it has preferentially to be understood the absolute value of the age difference, wherein if the age difference is greater than a predefined age limit value a, then the contribution is zero, otherwise said contribution depends on the age difference in that the smaller the age difference, the higher the contribution, and inversely. In other words, the contribution of quantitative map values for biological objects whose age does not belong to a predefined age interval I (e.g. I=[As−σ, As+σ] is zero, while a contribution to the weighted mean of quantitative maps for biological objects whose age belongs to the predefined age interval I depends on the age difference. To that end and preferentially, a kernel (e.g. Gaussian Kernel) is used to only take into account, for the averaging, the quantitative maps, for instance the quantitative maps acquired at step 101 or the registered quantitative maps obtained at the end of the iterative process of step 104 when steps 102-104 take place, for biological objects with an age that is within the predefined age interval I with respect to the specific age As, the specific age As corresponding for instance to the age of the investigated biological object (e.g. the predefined age interval might be obtained by taking σ=2 years when considering the Gaussian Kernel). In other words, the age-specific initial map is generated by the system for the specific age by averaging the intensities across the previously acquired or obtained quantitative maps (for instance, the quantitative maps acquired at step 101 or the registered quantitative maps obtained at the end of the iterative process of step 104 when steps 102-104 take place), wherein, for each of the previously acquired or obtained quantitative map for a biological object, the contribution to the average (i.e. a weight) depends on a difference (i.e. said age difference) between the specific age and the age of the biological object from which the previously acquired or obtained quantitative map is acquired or obtained (i.e. difference in atlas specific age and healthy subject age) and the chosen kernel (e.g. Gaussian with σ=2 years).

At step 106, each of the quantitative maps acquired at step 101 or each of the registered quantitative maps obtained at the end of the iterative process of step 104 when steps 102-104 take place is further spatially registered on the age-specific initial map using for instance a non-rigid registration. Advantageously, the non-rigid registration enables performing a localized morphing.

At step 107, the steps 105 and 106 are iteratively repeated so that at each iteration a new age-specific initial map is created using the weighted mean of the values of the registered quantitative maps obtained at the previous step. A contribution to the average when averaging the intensities across the previously obtained registered quantitative maps (i.e. the quantitative maps obtained at the previous step) depends on the age difference as explained in step 105, and optionally the chosen kernel. The previously registered quantitative maps obtained at the end of step 106 are then registered on the new age-specific initial map until reaching another predefined alignment threshold between all registered quantitative maps. The process of creating age-specific atlases (i.e. maps) and registrations (preferentially non-rigid registrations) is thus repeated iteratively to improve the alignment of the different biological object sub-structures until the another predefined alignment threshold is obtained. The predefined alignment threshold and the another predefined alignment threshold might be identical and preferentially predefined by an operator and stored in a database of the system according to the invention.

At step 108, the system stores the new age-specific initial map obtained at the end of the iterative process of step 107 as the age-specific quantitative atlas for a biological object characterized by the specific age. The new age-specific initial map obtained at the end of the iterative process of step 107 is therefore an age-specific quantitative atlas which provides for instance an expected mean and standard deviation for a biological object within the predefined interval. Such an age-specific quantitative atlas might be obtained for any age within the range of ages of the subjects of the healthy subject population using aligned (registered) quantitative maps and the previously described weighted mean (i.e. using the same kernel such as the Gaussian kernel).

Contrary to other techniques for creating a quantitative map, the present method is able to ensure that the biological object shape in the atlas corresponds to the typical shape of said biological object for that specific age.

Advantageously, the obtained age-specific quantitative atlas not only accounts for age-dependent changes in the microstructural tissue property (e.g. relaxation), but also in the macrostructural shape of the biological object. The proposed method facilitates the generation of more specific atlases which may help a physician to detect smaller pathological changes in comparison to conventional atlases.

In particular, the previously described iterative process improves the creation of quantitative atlases by making the latter age-specific, wherein intermediate results with a weighted mean across the healthy subjects might be generated in conjunction with a preferentially non-rigid registration.

The quantitative maps might be for instance maps of relaxation times T1 and T2. Other quantitative maps that might be used according to the present invention are for instance: apparent transverse relaxation T2*, proton density PD, inhomogeneous and homogeneous magnetization transfer, diffusion effects, multi-compartment data (e.g. fat fraction, myelin fraction), Hounsfield maps and others. The method can be further used on a combination of the quantitative values obtained by means of the previously mentioned quantitative maps. For example, a multiplication of PD and T1 may even yield an improved registration.

The biological object might be any organ which has both micro- and macrostructural changes depending on age. Apart from the brain, other biological objects would be for instance: liver, pancreas, prostate, heart and joints.

While preferentially an affine and then non-rigid registration are subsequently applied according to the previously described method, the type of registrations (affine and non-rigid) may be exchanged or replaced by another type (e.g. rigid registration). Optionally, the affine registration, i.e. steps 102-104, may be ignored. In such a case, the method comprises steps 101, 105-108, wherein the quantitative maps instead of the previously registered maps are directly used for creating the age-specific initial map.

Alternatively, the quantitative maps are weighted images obtained through conventional magnetic resonance imaging. In this case, microstructural information would not be present, but an age-specific atlas on the weighted images would advantageously provide reliable shape information for the biological object under investigation.

FIG. 2 illustrates a system 200 for creating an age-specific quantitative atlas for a biological object. The system includes a device 201 for acquiring a quantitative map for the biological object. The device being for instance a magnetic resonance imaging apparatus configured for acquiring quantitative maps for the biological object, e.g. brain images of a subject. A database 202 or memory is provided for storing data required for creating and storing the age-specific quantitative atlas. A processing unit 203 is configured for processing the data required for creating the age-specific quantitative atlas. Optionally, a display 204 is provided for displaying the age-specific quantitative atlas. The system 200 according to the invention is configured for performing the steps of the previously described method for creating said age-specific quantitative atlas.

The method and system according to the invention might be further configured for automatically comparing a quantitative map obtained for a biological object under investigation to an age-specific quantitative atlas as previously obtained, which is therefore specifically, and preferentially automatically, created for the age of the biological object under investigation, leading therefore to a better differentiation between age effects and disease effects.

In summary, the proposed invention enables the creation of an age-specific quantitative atlas that takes into account not only age-dependent, microstructural biological object changes, but also changes of the macrostructural biological object shape, creating therefore a more precise quantitative atlas that makes small pathological changes detectable.

The invention claimed is:

1. A method for creating an age-specific quantitative atlas for a biological object, the method comprises the following steps of:

obtaining a quantitative map of the biological object for each subject of a healthy subject population, wherein for each said quantitative map obtained during the obtaining step, a contribution to an average depends on a difference between a specific age and an age of the biological object from which quantitative maps obtained during the obtaining step have been obtained;

generating an age-specific initial map for the biological object using a weighted mean of intensities of the quantitative maps obtained by the obtaining step, wherein the age-specific initial map is generated for the specific age;

spatially registering each of the quantitative maps obtained by the obtaining step on the age-specific initial map;

repeating the generating and spatially registering steps iteratively so that at each iteration:
- a new age-specific initial map is created from the quantitative maps obtained at an end of a previous spatial registration step;
- the quantitative maps obtained at the end of the previous spatial registration step are then further registered on the new age-specific initial map; and
- performing the repeating step until reaching a first predefined alignment threshold between all spatially registered quantitative maps; and storing the new age-specific initial map obtained at an end of an iterative process of the repeating step as the age-specific quantitative atlas for the biological object characterized by the specific age.

2. The method according to claim 1, wherein if the difference is greater than a predefined age limit value, then the contribution is zero, otherwise the contribution depends on the difference in that a smaller said difference, a higher the contribution.

3. The method according to claim 1, wherein a kernel is used for a generation of the age-specific initial map.

4. A method for creating an age-specific quantitative atlas for a biological object, the method comprises the following steps of:

obtaining a quantitative map of the biological object for each subject of a healthy subject population;

creating an initial map by averaging quantitative map intensities across all quantitative maps obtained in the obtaining step;

spatially registering on the initial map each of the quantitative maps obtained in the obtaining step;

performing an iteration process by repeating the creating and the spatially registering on the initial map steps iteratively so that at each iteration:
- a new initial map is created by averaging the quantitative map intensities across all previously registered quantitative maps; and
- the previously registered quantitative maps are then spatially registered on the new initial map;

performing the iteration process until reaching a second predefined alignment threshold between all registered quantitative maps, the registered quantitative maps obtained at an end of the iteration process being then used for carrying out the generating and spatially registering steps performed on the quantitative maps, wherein the registered quantitative maps obtained at the end of the iteration process are the quantitative maps obtained at the previous step when carrying out the generating and spatially registering steps performed on the quantitative maps;

generating an age-specific initial map for the biological object using a weighted mean of intensities of the quantitative maps obtained by the obtaining step, wherein the age-specific initial map is generated for a specific age;

spatially registering each of the quantitative maps obtained by the obtaining step on the age-specific initial map;

repeating the generating and spatially registering steps iteratively so that at each iteration:
- a new age-specific initial map is created from the quantitative maps obtained at an end of a previous spatial registration step;
- the quantitative maps obtained at the end of the previous spatial registration step are then further registered on the new age-specific initial map; and
- performing the repeating step until reaching a first predefined alignment threshold between all spatially registered quantitative maps; and storing the new age-specific initial map obtained at an end of an iterative process of the repeating step as the age-specific quantitative atlas for the biological object characterized by the specific age.

5. A method for comparing quantitative values of a parameter measured for an investigated biological object characterized by a specific age with quantitative values of the parameter obtained for an age-specific quantitative atlas, the method comprises the steps of:

automatically creating the age-specific quantitative atlas for the parameter by the substeps of:
- obtaining a quantitative map of a biological object for each subject of a healthy subject population, wherein for each said quantitative map obtained during the obtaining step, a contribution to an average depends on a difference between the specific age and an age of the biological object from which quantitative maps obtained during the obtaining step have been obtained;
- generating an age-specific initial map for the biological object using a weighted mean of intensities of the quantitative maps obtained by the obtaining steps, wherein the age-specific initial map is generated for the specific age;
- spatially registering each of the quantitative maps obtained by the obtaining step on the age-specific initial map;
- repeating the generating and spatially registering steps iteratively so that at each iteration:
  - a new age-specific initial map is created from the quantitative maps obtained at an end of a previous spatial registration step;
  - the quantitative maps obtained at the end of the previous spatial registration step are then further registered on the new age-specific initial map; and
  - performing the repeating step until reaching a first predefined alignment threshold between all spatially registered quantitative maps;
- storing the new age-specific initial map obtained at an end of an iterative process of the repeating step as the age-specific quantitative atlas for the biological object characterized by the specific age;

acquiring the quantitative map of the investigated biological object for the parameter resulting in an acquired quantitative map; and automatically comparing the acquired quantitative map with the age-specific atlas in order to show differences between parameter values of the acquired quantitative map with respect to the age-specific atlas.

6. The method according to claim 5, wherein the acquiring step takes place automatically.

7. A system for creating an age-specific quantitative atlas for a biological object, the system comprising:

a device for acquiring a quantitative map for the biological object;

a database for storing data required for creating and storing the age-specific quantitative atlas;

a processor configured for processing the data required for creating the age-specific quantitative atlas;

wherein the system is configured to perform a method for creating the age-specific quantitative atlas for the biological object, the method comprises the following steps of:

obtaining the quantitative map of the biological object for each subject of a healthy subject population;

generating an age-specific initial map for the biological object using a weighted mean of intensities of quantitative maps obtained by the obtaining steps, wherein the age-specific initial map is generated for a specific age;

spatially registering each of the quantitative maps obtained by the obtaining step on the age-specific initial map;

repeating the generating and spatially registering steps iteratively so that at each iteration:

a new age-specific initial map is created from the quantitative maps obtained at an end of a previous spatial registration step; and the quantitative maps obtained at the end of the previous spatial registration step are then further registered on the new age-specific initial map;

performing the repeating step until reaching a first predefined alignment threshold between all spatially registered quantitative maps; and storing the new age-specific initial map obtained at an end of the iterative process of the repeating step as the age-specific quantitative atlas for the biological object characterized by the specific age;

wherein the system being further configured for comparing quantitative values of a parameter measured for an investigated biological object characterized by a specific age with quantitative values of the parameter obtained for the age-specific quantitative atlas, the system being further configured for:

automatically creating the age-specific quantitative atlas for the parameter;

automatically acquiring the quantitative map of the investigated biological object for the parameter; and automatically comparing an acquired quantitative map with the age-specific atlas in order to show differences between parameter values of the quantitative map with respect to the age-specific quantitative atlas.

8. The system according to claim 7, further comprising a display for displaying the age-specific quantitative atlas.

* * * * *